United States Patent [19]

Baker et al.

[11] 4,117,229

[45] Sep. 26, 1978

[54] 2-AMINO-1-(5-AMINO-1H-IMIDAZOL-4-YL)ETHANONE AND METHOD OF PREPARATION

[75] Inventors: David C. Baker; Sterling R. Putt, both of Ann Arbor, Mich.

[73] Assignee: Warner-Lambert Company, Morris Plains, N.J.

[21] Appl. No.: 841,098

[22] Filed: Oct. 11, 1977

[51] Int. Cl.$^2$ .............................................. C07D 233/88
[52] U.S. Cl. ..................... 548/301; 536/24; 542/405; 548/323; 548/339
[58] Field of Search ......................................... 548/301

[56] References Cited

U.S. PATENT DOCUMENTS 3,670,007   6/1972   Ferris .................................. 548/301

OTHER PUBLICATIONS

Stevens et al., Chem. Abst., 1962, vol. 57, col. 2216.
Tamamusi, Chem. Abst., 1940, vol. 34, col. 5446.

*Primary Examiner*—Natalie Trousof
*Attorney, Agent, or Firm*—Stephen Raines; David B. Ehrlinger; Frank S. Chow

[57] ABSTRACT

2-Amino-1-(5-amino-1H-imidazol-4-yl)ethanone, 6,7-dihydroimidazo[4,5-d][1,3]diazepin-8(3H)-one and acid-addition salts thereof are disclosed. 2-Amino-1-(5-amino-1H-imidazol-4-yl)ethanone and its acid-addition salts are prepared by catalytically reducing an acid-addition salt of 2-amino-1-[5-amino-1-(protected)-1H-imidazol-4-yl]ethanone. 6,7-Dihydroimidazo[4,5-d][1,3]-diazepin-8(3H)-one and its acid-addition salts are prepared by reacting an acid-addition salt of 2-amino-1-(5-amino-1H-imidazol-4-yl)ethanone with a compound able to contribute a formyl group. The later product may subsequently be converted into (R)-3-(2-deoxy-β-D-erythro-pentofuranosyl)-3,6,7,8-tetrahydroimidazo[4,5-d][1,3]diazepin-8-ol. Furanose derivatives of 6,7-dihydroimidazo[4,5-d][1,3]diazepine are also disclosed and their methods of preparation. Lastly, a method for resolving an isomer mixture of 3-(2-deoxy-β-D-erythro-pentafuranosyl)-3,6,7,8-tetrahydroimidazo[4,5-d][1,3]diazepin-8-ol compounds is related.

3 Claims, No Drawings

2-AMINO-1-(5-AMINO-1H-IMIDAZOL-4-YL)ETHANONE AND METHOD OF PREPARATION

SUMMARY AND DETAILED DESCRIPTION

The present invention relates to new imidazoles. More particularly, the invention relates to new imidazoles of the formulae

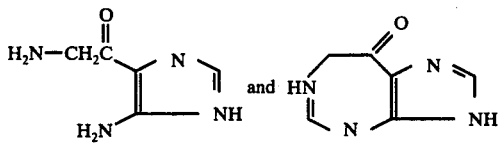

and acid-addition salts thereof. The preferred compounds are the new imidazoles in the form of their acid-addition salts since the free bases are of a low order of stability under ordinary circumstances.

The invention also relates to furanose derivatives of 6,7-dihydroimidazo[4,5-d][1,3]diazepines having the formula

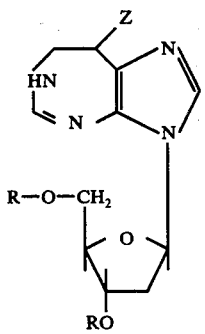

and acid-addition salts thereof wherein Z is ~OH or =O and R is hydrogen or Acyl.

In addition, the invention relates to methods for producing these new imidazole compounds and a method employing these new imidazole compounds in preparing (R)-3-(2-deoxy-β-D-erythropentofuranosyl)-3,6,7,8-tetrahydroimidazo[4,5-d][1,3]diazepin-8-ol (pentostatin).

In accordance with the invention, acid-addition salts of 6,7-dihydroimidazo[4,5-d][1,3]diazepin-8(3H)-one can be produced by reacting a di-acid-addition salt of 2-amino-1-(5-amino-1H-imidazol-4-yl)ethanone with a compound capable of donating a formyl group, such as (lower alkyl-O)₃CH, (acyl-O) (HN=)CH.HX, (lower alkyl-O)(HN=)CH.HX, (NH₂)(HN=)CH.HX, etc. wherein X is an anion.

The preferred formylating reagents are methyl or ethyl orthoformate and X being chloride.

The reaction is generally carried out in a lower alkyl alcohol, preferably ethanol, although other solvents may also be used such as dimethylsulfoxide, N,N-dimethylformamide or N,N-dimethylacetamide or mixtures of the above named solvents. While time and temperature may be varied, a range of about 50° C. to about 150° C. for about 30 minutes to about 6 hours is generally employed, preferably 75° C. to 85° C. for 1 to 2 hours. While the ratio of reactants is not critical, an excess of the formylating agent is generally preferred. The product is isolated in the form of its acid-addition salt, but may be converted to its relatively unstable free base by the addition of base, such as methanolic sodium hydroxide.

The term "lower alkyl" is intended to mean an alkyl group of from one to six carbon atoms, such as methyl, ethyl, butyl and isopentyl.

The term "acid-addition salt" is intended to mean a salt such as the hydrochloride, sulfate, acetate, benzoate, citrate, hydrobromide, nitrate, etc.

The term "Acyl" is intended to mean

wherein R is a relatively inert organic radical, preferably an organic radical having up to 12 carbon atoms.

Also in accordance with the invention, di-acid-addition salts of 2-amino-(5-amino-1H-imidazol-4-yl)ethanone may be prepared by catalytically reducing a di-acid-addition salt, preferably the dihydrochloride, of 2-amino-1-[5-amino-1-(arylmethyl)-1H-imidazol-4-yl]ethanone. The term "aryl" is intended to mean any aromatic group that facilitates the reductive cleavage of the adjacent CH₂ — N bond, preferably phenyl. The catalysts are generally noble metals such as Pd, Pt or Rh or oxides thereof. In addition, the catalyst may be supported on a carrier such as carbon with the preferred catalyst system being Pd-on-carbon. Hydrogen may be bubbled into the reaction medium or the reaction may be carried out in a hydrogen atmosphere at pressures of up to about four atmospheres. Generally polar solvents are employed such as water, lower alkyl alcohols, lower alkyl carboxylic acids or mixtures of the foregoing. A preferred solvent system uses water-methanol-acetic acid. While time and temperature are not critical, the reaction is generally conducted at a temperature range of about 15° C. to 35° C. until hydrogen absorption ceases. The product is isolated in the form of an acid-addition salt (usually two moles of acid per mole of imidazole compound). While the acid-addition salts, especially the di-acid salts, are preferred, the unstable free base may be prepared by the addition of a base.

The 2-amino-1-[5-amino-1-(arylmethyl)-1H-imidazol-4-yl]ethanone dihydrochloride is prepared by reducing a 2-nitro-1-[5-nitro-1-(arylmethyl)-1H-imidazol-4-yl]ethanone using stannous chloride dihydrate in concentrated hydrochloric acid.

The 2-nitro-1-[5-nitro-1-(arylmethyl)-1H-imidazol-4-yl]ethanones are prepared by first coupling a 5-nitro-1-(arylmethyl)-1H-imidazole-4-carboxylic acid to 1,1'-carbonyldiimidazole and reacting this product with the anion of nitromethane.

The 5-nitro-1-(arylmethyl)-1H-imidazole-4-carboxylic acids are prepared by treating (E)-5-nitro-4-(2-phenylethenyl)-1-(arylmethyl)-1H-imidazoles initially with ozone followed by performic acid.

The (E)-5-nitro-4-(2-phenylethenyl)-1-(arylmethyl)-1H-imidazoles are prepared by treating (E)-5-nitro-4-(2-phenylethenyl)-1H-imidazole [Ber. 56, 683 (1923)] with an arylmethyl bromide or iodide in the presence of anhydrous potassium carbonate.

This invention also relates to a method for converting the compounds of this invention into the potent deaminase inhibitor (R)-3-(2-deoxy-β-D-erythro-pentofuranosyl)-3,6,7,8-tetrahydroimidazo[4,5-D][1,3]diazepin-8-ol (pentostatin), which is the subject matter of U.S. Pat. No. 3,923,785, which is incorporated by reference. This deaminase inhibitor potentiates the activity of the known antiviral agent, 9-(β-D-arabinofuranosyl)adenine.

Thus in accordance with the invention, (R)-3-(2-deoxy-β-D-erythro-pentofuranosyl)-3,6,7,8-tetrahydroimidazo[4,5-D][1,3]diazepin-8-ol, having the structure

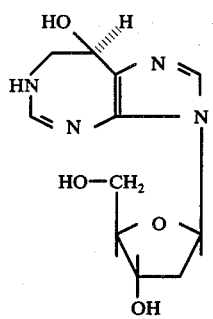

is separated from mixtures of two isomers having the following formula

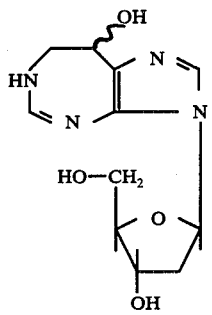

using a reverse-phase chromatographic procedure. A derivatized column of silica gel, wherein said derivative is a lipophilic moiety, perferably the octadecylsilyl derivative, is eluted with a polar solvent such as water, methanol, ethanol or mixtures thereof, preferably 95:5 water-methanol.

The isomer mixture may be obtained by reducing a compound of the invention having the formula

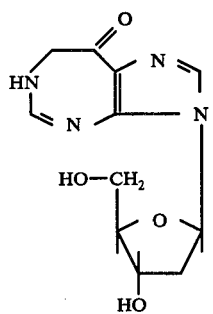

which has the name 3-(2-deoxy-β-D-erythro-pentofuranosyl)-3,6,7,8-tetrahydroimidazo[4,5-d][1,3]diazepin-8-one, or an acid-addition salt thereof. The reduction may preferably be achieved by using a borohydride, such as sodium borohydride, potassium borohydride, lithium borohydride, tetra(lower-alkyl)ammonium borohydride.

In addition, the reduction may be carried out employing diborane and its derivatives such as thexylborane, 9-borobicyclononane, etc., alkali metal derivatives of triloweralkyl boranes, such as lithium or potassium tri-sec-butylborane, or aluminum hydrides, such as lithium aluminum hydride, allane, di-lower alkylallane, sodium bis(2-methoxyethoxy)aluminum hydride.

The use of the above reagents in effecting the reduction is taught in the references: H.O. House, "Modern Synthetic Reactions," 2nd Edition, Benjamin (Menlo Park, Calif.), 1972, pp. 45–130 and C. A. Buehler and D. E. Pearson, "Survey of Organic Syntheses," Wiley-Interscience (New York), 1970, pp. 193–212, which are incorporated by reference.

In addition, the ketone may be reduced using a catalyst in the presence of molecular hydrogen. Choice catalysts would be ruthenium, platinum, platinum oxide, palladium, copper chromite, certain transition-metal complexes, etc. The catalysts may be on standard supports, such as carbon.

The use of catalytic processes is reported in the following references: R. L. Augustine, "Catalytic Hydrogenation," Marcel Dekker (New York), 1965, pp. 81–88 and C. A. Buehler and D. E. Pearson, "Survey of Organic Syntheses," Wiley-Interscience (New York), 1970, p. 201, which are incorporated by reference.

The compound of the formula

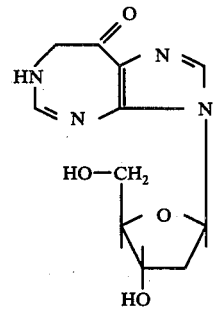

is prepared by deprotecting a compound of the formula

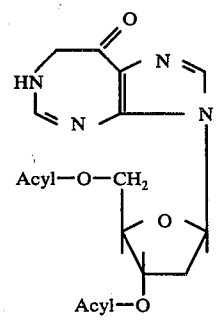

using a strong base, preferably an alkali metal lower alkoxide such as sodium methoxide in a polar solvent, preferably an alcohol such as methanol. The reaction is carried out in a time period of from a few minutes to about 3 hours at from about 0° C. to about 70° C.

In addition, the mixture of two isomers having the following formula

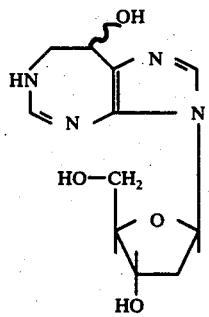

may be obtained by deprotecting a compound of the invention having the formula

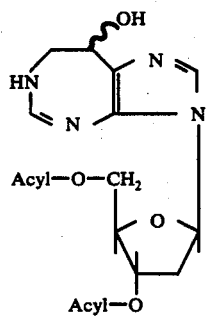

which has the name 6,7-dihydro-3-[3,5-di-O-(p-toluoyl)-α,β-D-erythro-pentofuranosyl]-imidazo[4,5-d][1,3]-diazepin-8(3H)ol, or an acid-addition salt thereof wherein acyl is as previously defined and is preferably p-methylbenzoyl. The deprotection is carried out employing a strong base in a polar solvent at temperatures from about 0° C. to about 50° C., preferably 25° C., for periods of from about a few minutes to about 12 hours, preferably 1 hour.

The preferred base is an alkali metal lower alkoxide, such as sodium methoxide, in an alcohol, such as methanol.

The foregoing di-acyl protected compound is prepared by reducing a compound having the formula

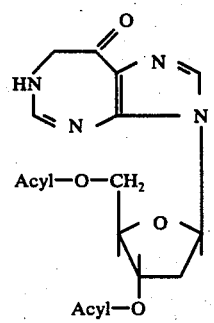

wherein Acyl is as previously defined and is preferably p-methylbenzoyl. The same reduction procedures given earlier for the reduction of compounds of the formula are employed.

The preferred process utilizes sodium borohydride in a polar solvent such as water, lower alkyl alcohols or mixtures thereof. Temperatures of from 0° C. to 50° C. for periods of from a few minutes to about 3 hours are generally employed.

The compound of the formula

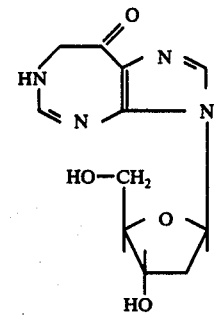

The compound of the formula

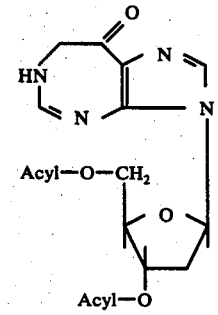

wherein Acyl is as previously defined and preferably p-methylbenzoyl is prepared by coupling a compound of the formula

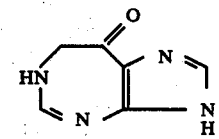

in the presence of bis(trimethylsilyl)acetamide, with a compound of the formula

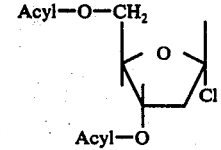

The invention is illustrated by the following examples.

EXAMPLE 1

2-Amino-1-(5-amino-1H-imidazol-4-yl)ethanone dihydrochloride

A solution of 1.0 g. of 2-amino-1-[5-amino-1-(phenylmethyl)-1H-imidazol-4-yl]ethanone dihydrochloride in 100 ml. of 70:20:10 methanol:water:acetic acid is hydrogenated over 0.52 g. of 20% palladium-on-carbon at 50 p.s.i. until hydrogen uptake ceases. The catalyst is removed by filtration and the filtrate is evaporated at reduced pressure to give 2-amino-1-(5-amino-1H-imidazol-4-yl)ethanone dihydrochloride; m.p. above 250° dec.

INTERMEDIATES a. Mixture of (E)-5-nitro-4-(2-phenylethenyl)-1-(phenylmethyl)-1H-imidazole and (E)-4-nitro-5-(2-phenylethenyl)-1-(phenylmethyl)-1H-imidazole A well-stirred suspension of 215.2 g. of (E)-5-nitro-4-(2-phenylethenyl)-1H-imidazole [Ber., 56, 683 (1923)] in 1.6 l. of dry dimethylformamide, protected from moisture, is treated in turn with 207.3 g. of anhydrous potassium carbonate, then with 205 g. of benzyl bromide over a 15 minute period. The mixture is stirred and heated at 75° C. for 2 hours, then cooled to about 15° C. and filtered. The filter cake of inorganic salts is washed well with dichloromethane. The filtrate and washings are combined and evaporated at reduced pressure. The residual oil is evaporated several times with xylene under reduced pressure to remove traces of dimethylformamide. The residue is partitioned between 500 ml. of water and 2 l. of dichloromethane. The organic phase is separated, dried and evaporated. The residual partially crystalline mass is dissolved in a minimum amount of boiling chloroform. The hot chloroform solution is diluted with 7 l. of boiling cyclohexane, then treated with a small amount of chloroform to clarify the cloudiness. The resulting solution is cooled slowly, with vigorous stirring, to 5° C. The crystalline precipitate consisting of a 3:1 mixture of (E)-5-nitro-4-(2-phenylethenyl)-1-(phenylmethyl)-1H-imidazole and (E)-4-nitro-5-(2-phenylethenyl)-1-(phenylmethyl)-1H-imidazole is collected by filtration, washed with cyclohexane and dried; m.p. 90°-92° C.

b. 5-Nitro-1-(phenylmethyl)-1H-imidazole-4-carboxylic acid

A stream of 6% ozone in dry oxygen is bubbled at a rate of 1.7 l./minute into a solution of 138.6 g. of a 3:1 mixture of (E)-5-nitro-4-(2-phenylethenyl)-1-(phenylmethyl)-1H-imidazole and (E)-4-nitro-5-(2-phenylethenyl)-1-(phenylmethyl)-1H-imidazole in 2.3 l. of dichloromethane at −78° C. for 5 hours, while protecting the system from moisture. An excess of ozone is present as evidenced by its blue color. The solution is allowed to warm to −30° C., while removing the excess ozone by a dry nitrogen purge. The solution is then evaporated at reduced pressure and the residual oil dissolved promptly in 433 ml. of 97% formic acid. The formic acid solution is treated dropwise, with stirring and cooling to 0°-5° C., with 173 ml. of 30% hydrogen peroxide. The mixture is stirred at room temperature for 16 hours and the resulting precipitate is collected by filtration and washed with water. The solid is suspended in 5 l. of water and the pH is adjusted to 10-11 with concentrated aqueous ammonia. After stirring 1 hour, the solution is filtered to remove insolubles. The pH of the filtrate is adjusted to 2 with concentrated hydrochloric acid. The resulting precipitate of 5-nitro-1-(phenylmethyl)-1H-imidazole-4-carboxylic acid is collected by filtration, washed well with water and dried; m.p. 151°-152° C.

c. 2-Nitro-1-[5-nitro-1-(phenylmethyl)-1H-imidazol-4-yl]ethanone

A mixture of 67.8 g. of 5-nitro-1-(phenylmethyl)-1H-imidazole-4-carboxylic acid and 72.9 g. of 1,1′-carbonyldiimidazole in 800 ml. of dry tetrahydrofuran, protected from moisture, is heated at reflux for 1 hour. The resulting solution is evaporated at reduced pressure and the residual oil is dissolved in 450 ml. of dichloromethane. The solution is washed quickly with 100 ml. of ice water, dried promptly and evaporated at reduced pressure to give the imidazolide. A solution of this imidazolide in 800 ml. of tetrahydrofuran is added dropwise, with vigorous stirring, to a solution of 36.9 g. of potassium tert-butoxide and 65 ml. of nitromethane in 600 ml. of tetrahydrofuran, with the exclusion of moisture. The mixture is stirred at room temperature for 16 hours and the resulting solid collected by filtration and washed thoroughly with dichloromethane. The solid is suspended in 600 ml. of water and the pH adjusted to 3 with concentrated hydrochloric acid. The suspension is repeatedly extracted with 200 ml. portions of ethyl acetate, with the pH being readjusted to 3 before each extraction. The combined extract is dried, decolorized with activated charcoal and evaporated at reduced pressure to give 2-nitro-1-[5-nitro-1-(phenylmethyl)-1H-imidazol-4-yl]ethanone; m.p. 105°-107° C.

d. 2-Amino-1-[5-amino-1-(phenylmethyl)-1H-imidazol-4-yl]-ethanone dihydrochloride A stirred solution of 38 g. of stannous chloride dihydrate in 100 ml. of concentrated hydrochloric acid is treated portionwise with 10 g. of 2-nitro-1-[5-nitro-1-(phenylmethyl)-1H-imidazol-4-yl]ethanone. Ten ml. of ethanol are added to clarify the solution and the mixture is stirred at 60° C. for 3 hours. The solution is evaporated to near dryness and three 100 ml. portions of ethanol are added sequentially and evaporated from the residue. The residual syrup is stirred with 800 ml. of ether and the resulting solid is collected by filtration, washed with ether and dried at reduced pressure. This solid (a tin complex) is dissolved in 150 ml. of water and the tin is precipitated as the sulfide by bubbling hydrogen sulfide gas into the solution. The mixture is filtered and the filter cake washed with water. The filtrate and washings are combined and evaporated at reduced pressure. The residue is repeatedly evaporated with 100 ml. portions of ethanol. The final residual gum is triturated with 30 ml. of ethanol to give as a crystalline solid 2-amino-1-[5-amino-1-(phenylmethyl)-1H-imidazol-4-yl]ethanone dihydrochloride, which is collected by filtration, washed with ethanol and dried at reduced pressure; m.p. 155° C. (dec.).

EXAMPLE 2

6,7-Dihydroimidazo[4,5-d][1,3]diazepin-8(3H)-one monohydrochloride

A mixture of 285 mg. of 2-amino-1-(5-amino-1H-imidazol-4-yl)ethanone dihydrochloride (Example 1), 200 ml. of absolute ethanol and 10 ml. of triethyl orthoformate is stirred and heated at reflux for 1 hour, then cooled and evaporated at reduced pressure. The residue of 6,7-dihydroimidazo[4,5-d][1,3]diazepin-8(3H)-one monohydrochloride, which crystallizes on standing, is collected by filtration, washed with ethanol, then with ether, and dried at reduced pressure; m.p. above 250° C. dec.

EXAMPLE 3

6,7-Dihydro-3-[3,5-di-O-(p-toluoyl)-α,β-D-erythro-pentofuranosyl]-imidazo[4,5-d][1,3]diazepin-8(3H)-one A suspension of 450 mg. of 6,7-dihydroimidazo[4,5-d]-[1,3]diazepin-8(3H)-one monohydrochloride (Example 2) in 5 ml. of acetonitrile is treated with 2 ml. of bis(trimethylsilyl)acetamide, stirred at room temperature for 16 hours, then evaporated at reduced pressure. The residue is dissolved in 5 ml. of dry 1,2-dichloroethane and the solution is treated with 1.0 g. of 3,5-di-O-(p-toluoyl)-α-D-erythro-pentofuranosyl chloride [Ber., 93, 2777 (1960)]. The resulting solution is evaporated at reduced pressure. The residue is then heated at 80°–110° C. under reduced pressure for 1 hour. The residue is dissolved in a mixture of 25 ml. of ethyl acetate and 25 ml. of saturated aqueous sodium bicarbonate and the two-phase system is clarified by filtration. The filtration is evaporated at reduced pressure and the residue is applied to the top of a 1.9 × 60 cm. column of silica gel. The column is eluted with a gradient of 500 ml. of ethyl acetate to 500 ml. of 9:1 ethyl acetate/methanol, while collecting 4-ml. fractions. Those fractions (nos. 45–58) containing the desired product (as determined by TLC) are combined and evaporated at reduced pressure to give 6,7-dihydro-3-[3,5-di-O(p-toluoyl-α,β-D-erythro-pentofuranosyl]imidazo[4,5-d][1,3]diazepin-8(3H)-one.

EXAMPLE 4

Mixture containing (R)-3-(2-deoxy-α-D-erythro-pentofuranosyl)-3,6,7,8-tetrahydroimidazo[4,5-d][1,3]diazepin-8-ol (pentostatin)

A solution of 25 mg. of 6,7-dihydro-3-[3,5-di-O-(p-toluoyl)-60 ,β-D-erythro-pentofuranosyl]imidazo[4,5-d][1,3]diazepin-8(3H)-one in 5 ml. of ethanol is treated with 10 mg. of sodium borohydride and stirred at room temperature for 15 minutes. About 5 mg. of sodium is then added, the solution is stirred at room temperature for 15 minutes, then neutralized with carbon dioxide. The mixture is evaporated at reduced pressure and the residue is partitioned between 10 ml. of ether and 10 ml. of water. The aqueous phase is separated and evaporated at reduced pressure. The residue is applied to the top of a 1 × 10 cm. column of Dowex 50×2 resin (a strongly acidic cation exchange resin) in the ammonium form. The resin is eluted with 25 ml. of 0.01N aqueous ammonia and the eluate is evaporated at reduced pressure to give a residue consisting of a mixture of the four possible isomers, one of which is (R)-3-(2-deoxy-β-D-erythro-pentofuranosyl)-3,6,7,8-tetrahydroimidazo[4,5-d][1,3]diazepin-8-ol (pentostatin).

EXAMPLE 5

6,7-Dihydro-3-[3,5-di-O-(p-toluoyl)-β-D-erythro-pentofuranosyl]-imidazo[4,5-d][1,3]diazepin-8(3H)-one Bis(trimethylsilyl)acetamide, 68 ml., is added to 11.20 g. of 6,7-dihydroimidazo[4,5-d][1,3]diazepin-8(3H)-one hydrochloride suspended in 112 ml. of acetonitrile and the mixture is stirred, under dry conditions for 0.5 hours, at the end of which time the excess reagent is removed at 40° C./0.1 mm. A solution of 24.23 g. of 3,5-di-o-(p-toluoyl)-α-D-erythro-pentofuranosyl chloride in 30 ml. of dry 1,2-dichloroethane is added to the syrupy (trimethyl)silylated heterocycle, and the solvent is evaporated. The resulting gum is fused at 100°/10 mm. for 24 minutes, at the end of which time the reaction mixture is triurated in 300 ml. of aqueous sodium bicarbonate solution for about 0.5 hours, then extracted with 200 ml. of ethyl acetate. The magnesium sulfate dried extract is passed across a column of 250 g. of silica gel and eluted sequentially with 1 liter each of ethyl acetate, 5%, 10% and 15% methanolic ethyl acetate. The desired products elutes with the 10% methanolic solvent. The solvent is removed by evaporation in vacuo, and the α product is crystallized from 150 ml. of hot ethyl acetate (m.p. 220° dec).

The mother liquors were evaporated, and from warm ethyl acetate was deposited crystals of the above named β-anomer (m.p. 129° C., softens and melts at 155° C.).

EXAMPLE 6

6,7-Dihydro-3-(β-D-erythro-pentofuranosyl)imidazo[4,5-d][1,3]diazepin-8(3H)-one

Metallic sodium (25 mg.) is added to a suspension of 1.52 g. of the 6,7-dihydro-3-[3,5-di-O-(p-toluoyl)-β-D-erythropentofuranosyl]imidazo[4,5-d][1,3]diazepin-8(3H)-one in 30 ml. of dry methanol. The mixture soon goes into solution, and analysis by tlc (silica gel, 9:1 chloroform-methanol) indicated complete reaction to give the free nucleoside within 45 minutes at 23°–25°. Solid carbon dioxide is added to neutralize the base, and the mixture is vaporated to dryness. The residue is extracted with ether and dried in vacuo to give a mixture of the nucleoside and sodium carbonate; $\lambda^{MeOH}_{max}$ = 232 (E'.442), 298 (57) and 346 nm. (92); the E' shows ca. 50% nucleoside in the salt-nucleoside mixture.

EXAMPLE 7

3-(2-Deoxy-β-D-erythro-pentofuranosyl)-3,6,7,8-tetrahydroimidazo[4,5-d][1,3]diazepin-8ol The crude nucleoside obtained in Example 6 is dissolved in 50 ml. of water and 60 mg. of sodium borohydride is added, portionwise, with stirring. After 40 minutes, the excess reducing agent is decomposed by the addition of solid carbon dioxide, and the solution is lyophilized to dryness. The salts are removed by chromatography over SP-Sephadex [NH$_4^+$] [a sulfonylpropyl-derivatized dextran polymer; alternatively a sulfonic acid resin such as Dowex-50 [NH$_4^+$] can be used]; elution was with water, then with 0.01N ammonium hydroxide, which caused immediate elution of R— and S— forms of the above compound.

EXAMPLE 8

(R)-3-(2-deoxy-β-D-erythro-pentofuranosyl)-3,6,7,8-tetrahydroimidazo[4,5-d][1,3]diazepin-8-ol The mixture of R and S-nucleoside isomers obtained in Example 7 is loaded onto a 0.9×60 cm. column of a reverse-phase octadecylsilyl-derivatized column of silica gel and eluted with 95:5 water-methanol. After 20 minutes of elution (5.5 ml./minute, 2000 psi) the S-isomer appears, followed by the R-isomer at 25.5 minutes. The products are isolated as lyophilized powders. R-isomer:

$[\alpha]_D^{23}$ = +76°, $[\alpha]_{365}^{23}$ = +630° (c 1, water)

We claim:

1. A compound having the name 2-amino-1-(5-amino-1H-imidazol-4-yl)ethanone and acid-addition salts thereof.

2. The compound of claim 1 wherein said acid-addition salt is the dihydrochloride.

3. A process for the preparation of a compound of claim 1 which comprises reducing 2-amino-1-[5-amino-1-(arylmethyl)-1H-imidazol-4-yl]ethanone or an acid-addition salt thereof.

* * * * *